(12) United States Patent
Haj-Ahmad

(10) Patent No.: US 7,026,453 B2
(45) Date of Patent: Apr. 11, 2006

(54) METHOD OF PROTEIN PURIFICATION

(75) Inventor: Yousef Haj-Ahmad, St. Catharines (CA)

(73) Assignee: Norgen Biotek Corporation, Ontario (CA)

( * ) Notice: Subject to any disclaimer, the term of this patent is extended or adjusted under 35 U.S.C. 154(b) by 414 days.

(21) Appl. No.: 10/294,283

(22) Filed: Nov. 13, 2002

(65) Prior Publication Data
US 2003/0114648 A1    Jun. 19, 2003

Related U.S. Application Data

(60) Provisional application No. 60/331,464, filed on Nov. 16, 2001.

(51) Int. Cl.
*C07K 1/00* (2006.01)
*C12P 21/06* (2006.01)

(52) U.S. Cl. ................ 530/361; 530/362; 530/363; 435/69.1; 435/172.3

(58) Field of Classification Search ................ 530/361, 530/362, 363; 435/69.1, 172.3
See application file for complete search history.

(56) References Cited

U.S. PATENT DOCUMENTS

| 5,098,576 A | 3/1992 | Cabrera et al. |
| 5,459,253 A | 10/1995 | Wolin et al. |
| 5,614,391 A | 3/1997 | Franciskovich et al. |
| 6,177,278 B1 | 1/2001 | Haj-Ahmad |

OTHER PUBLICATIONS

Keiki-Pua et al., J. Am. Chem. Soc., vol. 121, No. 34, pp. 7925-7930, 1999.*

* cited by examiner

*Primary Examiner*—Jon Weber
*Assistant Examiner*—Abdel A. Mohamed
(74) *Attorney, Agent, or Firm*—Myers, Bigel, Sibley & Sajovec, P.A.

(57) ABSTRACT

Purification methods are provided for proteins and peptides, employing silicon carbide to bind the proteins or peptides. The methods may also be used to recover and purify recombinantly expressed proteins sequestered in inclusion bodies. The method for purifying a protein or peptide comprises contacting a solution containing the protein or peptide with silicon carbide at a binding pH for the protein or peptide to allow the protein or peptide to bind to the silicon carbide; and eluting the protein or peptide from the silicon carbide.

26 Claims, 12 Drawing Sheets

METHOD OF PROTEIN PURIFICATION

RELATED APPLICATION INFORMATION

This application claims the benefit of U.S. Provisional Application No. 60/331,464, filed Nov. 16, 2001, which is incorporated by reference herein in its entirety.

FIELD OF THE INVENTION

The present invention relates to methods for purifying proteins and peptides and more particularly to protein and peptide purification methods employing silicon carbide.

BACKGROUND OF THE INVENTION

Purification of proteins from a heterogeneous mixture often involves a multi-step process that makes use of the physical, chemical and electrical properties of the protein being purified. Important properties of a protein that are relevant to its purification are (a) solubility, which determines the ability of the protein to remain in solution or to precipitate out in the presence of salt; (b) charge, which is an important property relevant to ion exchange chromatography and isoelectric focusing; (c) size, which is relevant in processes involving dialysis, gel-filtration chromatography, gel electrophoresis and sedimentation velocity; (d) specific binding, which allows purification of a protein based on its binding to a ligand; and (e) ability to form complexes in the presence of other reagents, such as in antibody precipitation. Protein detection and purification has become a major focus of research activities in view of the challenges faced by researchers involved in functional genomics and proteomics.

Popular chromatographic approaches may rely on a protein's ability to bind to a molecule linked to the matrix of a column, as in affinity chromatography, on the protein's size as in size exclusion or molecular sieving or on the pH at which the protein is electrically neutral such as in chromatofocusing or may utilize hydrophobic interactions as in reverse-phase chromatography or overall charge of the protein as in ion exchange chromatography. Since there are many different types of proteins and no single method has proved equally suitable for all proteins, it has become customary to combine different approaches to maximize yield and maintain the biological activity of the purified protein. Processes that simplify the purification of proteins with reductions in processing time remain much sought after for both large and small scale purifications.

A further area in which improved protein purification processes are greatly needed is in the recovery of recombinant proteins after expression in recombinant hosts, such as *E.coli*. The expression step may be highly efficient but thereafter there may be problems of improper protein folding and the protein may become sequestered within the host in inclusion bodies. Proteins in inclusion bodies are insoluble, tightly packed aggregates, generally lacking biological activity. Recovery of active proteins from inclusion bodies requires solubilization, refolding and purification of the recombinant protein product. These processes are often time-consuming and require customization for the specific protein being purified.

Silicon carbide has been shown to bind negatively charged macromolecules such as DNA and RNA. It has therefore been utilized for the purification of nucleic acid macromolecules, as described in U.S. Pat. No. 6,177,278, with many applications such as genetic research, gene therapy, genetic vaccination and cosmetics.

Protein purification methods employing interactions between proteins and silicon carbide have not been previously described.

SUMMARY OF THE INVENTION

New, convenient purification methods are provided for proteins and peptides, employing silicon carbide to bind the proteins or peptides. An improved method for recovering and purifying recombinantly expressed proteins which are sequestered in inclusion bodies is also provided.

In one embodiment, a method for recovering at least one protein or peptide from a solution comprising:

contacting the solution containing the at least one protein or peptide with silicon carbide at a binding pH for the at least one protein or peptide to allow the at least one protein or peptide to bind to the silicon carbide; and
eluting the at least one protein or peptide from the silicon carbide.

In a further embodiment, the binding pH is lower than the isoelectric point (pl) of the protein or peptide to be purified, preferably a pH at least about 0.5 pH units below the pl of the protein or peptide and greater than about pH 4. The elution pH is at least about 1 pH unit higher than the pl.

In a further embodiment, the protein or peptide is contacted with silicon carbide in the presence of a chaotrope and the binding pH is higher than the isoelectric point of the protein or peptide, preferably at least about 0.5 pH units above the pl.

In a further embodiment, a method for recovering total proteins from a complex mixture such as a cell lysate-comprises contacting the mixture with silicon carbide at a binding pH which is below the pl of the proteins to be recovered, to allow the proteins to bind to the silicon carbide, followed by elution at a pH above the pl of the proteins to be recovered.

In a further embodiment, a method of recovering and purifying a recombinant protein expressed in a recombinant host and sequestered in inclusion bodies and wherein the method comprises an initial step of contacting the inclusion bodies containing the recombinant protein with a solubilising agent to provide a solution containing the recombinant protein, followed by contacting the solution with the silicon carbide at a binding pH for the protein.

SUMMARY OF THE DRAWINGS

The present invention will be further understood from the following description with reference to the Figures, in which.

DETAILED DESCRIPTION OF THE INVENTION

Figure 1:
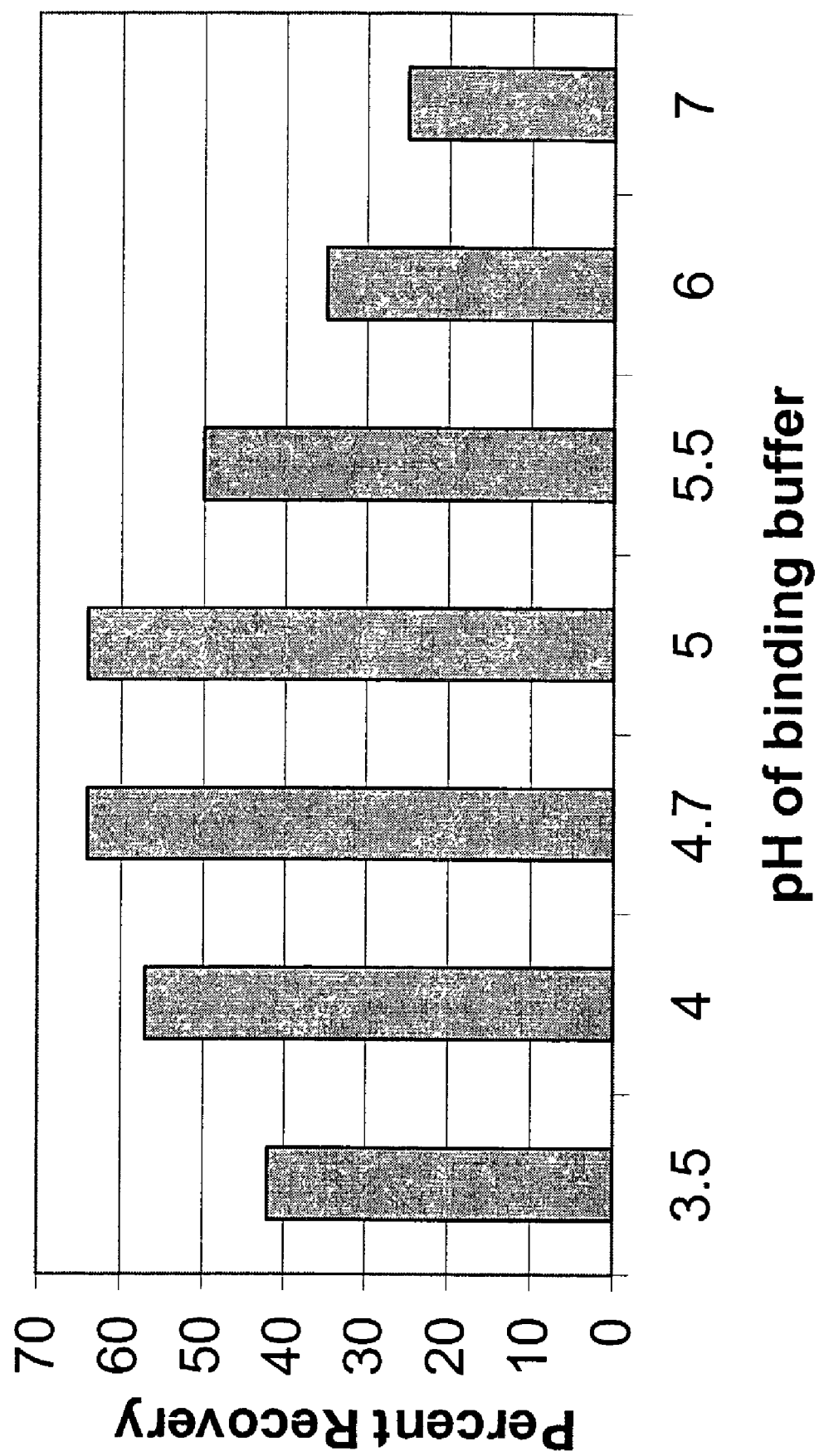
FIG. 1 shows the effect of binding pH on the recovery of BSA from silicon carbide. Y axis shows % protein recovered, relative to total input amount.

It has been found that proteins can be bound to and eluted from silicon carbide by manipulation of the pH of the proteins' environment and that this property can be employed to provide a new, simple and convenient method to recover a protein of interest from a mixture of proteins and/or other molecules, to concentrate a protein from a solution or to recover total proteins from a mixture such as a cell lysate. Peptides can also be similarly purified or recovered by the methods of the invention.

In accordance with the invention, silicon carbide is mixed with a solution containing a protein or peptide to be purified at "a binding pH", which means a pH at which the protein or peptide of interest binds to silicon carbide. The silicon carbide is then separated from the solution and the protein or peptide of interest is eluted from the silicon carbide by adjusting the pH to "an elution pH", which means a pH which facilitates elution of the protein or peptide from the silicon carbide. After binding of the protein or peptide, the silicon carbide may be washed with a buffer at the binding pH before elution of the protein or peptide.

In accordance with one embodiment, a solution of the protein or peptide of interest is contacted with silicon carbide at a binding pH which is a pH below the isoelectric point (pI) of the protein or peptide. Some protein binding will occur at the pI but a binding pH below the pI of the protein is preferred for more efficient binding. Any pH below the pI of the protein or peptide may be used as binding pH in this embodiment. The pH must not, however, be so low as to cause denaturation of the protein. For most proteins, a binding pH below the pI but greater than about pH 4 is preferred, although some proteins may be able to survive pH values below pH 4 without denaturation. A binding pH at least about 2 pH units below the pI, preferably at least about 1 pH unit below the pI and more preferably at least about 0.5 pH units below the pI of the protein or peptide but greater than about 4 is useful for a wide range of proteins and peptides.

A pH at least about two pH units and preferably at least about one pH unit higher than the pI of the protein is generally suitable as elution pH. The eluted protein may then be readjusted to a neutral pH. If a pH about 0.5 pH units higher than the pI of the protein is used as elution pH, elution is less efficient and multiple elutions are required.

The isoelectric point of a protein of interest may be determined by conventional methods such as by isoelectrofocusing in a polyacrylamide gel. The isoelectric point may also be approximated by predictive methods, by examining the amino acid composition of the protein and calculating the charge proportion of ionizable groups at various pH values, making use of the Henderson-Hasselbach equation (Lehninger "Principles of Biochemistry" (2000), D. C. Nelson and M. M. Cox., $3^{rd}$ Ed., Worth).

Alternatively, if a purified sample of the protein of interest is available, its binding properties to silicon carbide can be examined as described herein and a suitable binding pH to give optimal binding determined. Where a protein of interest is contained in a complex mixture of proteins, the optimal binding pH and elution pH for recovery of the protein can be determined as described herein.

In accordance with a further embodiment, a method is provided for quickly and conveniently recovering total proteins from a complex solution such as a cell lysate. The cell lysate or other solution containing a mixture of proteins is contacted with silicon carbide at a binding pH to allow the proteins to bind and the proteins are then eluted from the silicon carbide at an elution pH, as described above for recovery of a single protein. The binding pH should be lower than the pI of all of the proteins to be recovered. A binding pH of about 4.0 is suitable for binding most of the proteins in a typical cell lysate. The elution pH should be higher than the pI of all of the proteins to be eluted. An elution pH of about 12.0 is suitable for eluting most of the proteins in a typical cell lysate. This method is useful for analysing and comparing protein expression patterns in different cells, for example normal and pathogenic versions of a particular cell. Total proteins are quickly recovered from cell lysates as described above and can then be analysed by conventional 2D gel electrophoresis techniques. Cell lysates from which total proteins may be recovered by the method of the invention include lysates of mammalian, yeast and bacterial cells. For example, lysates of normal and cancerous mammalian cells may be subjected to the described method to recover proteins for further analysis.

In a preferred embodiment, the solution containing the protein to be purified is adjusted to a binding pH and the silicon carbide is pre-equilibrated in a buffer at that pH before mixing with the protein solution.

As will be understood by those of skill in the art, proteins and peptides may be purified by binding to silicon carbide using adaptations of a variety of purification techniques. The silicon carbide may be retained in a variety of supports.

For example, the method may be carried out by preparing a slurry of the protein-containing mixture and silicon carbide at a binding pH, followed by removal of the silicon carbide from the mixture after binding of the protein. Elution is carried out by preparing a slurry of the silicon carbide and elution solution.

Alternatively, the silicon carbide may be poured into a column, equilibrated to the binding pH either before or after the making of the column, and the solution containing the protein, adjusted to the binding pH, is passed over the column, in the same manner as is known for conventional column chromatography. After protein binding, elution is similarly carried out.

In a further embodiment, the silicon carbide, equilibrated to a binding pH, may be placed in a spin column, the solution containing the protein of interest, adjusted to a binding pH, is layered on to the top surface of the silicon carbide and the tube is centrifuged to separate the liquid phase, which is discarded. The silicon carbide with retained protein is washed, then contacted with a solution of buffer at an elution pH, followed by centrifugation to separate the liquid phase containing the eluted protein.

The use of spin columns allows a fast and convenient method of protein purification but many protein purification resins, such as agarose-based resins, cannot be employed in a spin column method as they are unable to withstand the required centrifugal forces. Silicon carbide, however, is a strong material which can withstand centrifugation and lends itself well to spin column techniques of purification.

The method of the invention may also be used in an adapted chromatofocusing technique. For example, a complex source of proteins is contacted with silicon carbide at a low binding pH using the column chromatography format. In this case, all proteins whose pI are below the binding pH will bind to silicon carbide. The bound proteins will then be eluted by passing the elution buffer at a high pH through the column. The passing of the elution buffer creates a pH gradient along the column's length so that the bound proteins will elute as the pH in the column reaches their pI. Fractions that are collected will contain different proteins.

In accordance with a further embodiment, it has been found that proteins may be purified by elution from silicon carbide after binding to the silicon carbide at a binding pH which is higher than the isoelectric point of the protein, a pH at which the protein is presumably negatively charged, by carrying out binding of the protein to the silicon carbide in the presence of a chaotrope at a non-denaturing concentration. Suitable chaotropes include guanidinium hydrochloride and sodium iodide. A binding pH higher than about 0.5 pH units above the pI is preferred.

Sodium iodide is used preferably at a concentration of up to 3M and guanidinium HCl preferably below 1M. The elution pH for this embodiment should be a high pH, preferably in the range of about 11.0 to about 12.0.

Purification of a protein by binding to silicon carbide at a pH higher than its isoelectric point, in the presence of a chaotrope, is preferred where the protein is acidic, for example with a pI of 4.0 to 4.5. An example of acidic proteins is the group of *Zea mays* phosphoproteins (P-proteins) that form a stalk structure in the 60S ribosomal subunit.

For such a protein, binding of the protein to silicon carbide at a binding pH lower than its pI, as earlier described, would require exposing the protein to potentially denaturing acid pH's. This can be avoided by binding in the presence of chaotrope at a pH above the pI, where the protein is likely to suffer less denaturation.

Purification of a protein whose pI is greater than about pH 9 (i.e., lysozyme) is preferably carried out by binding at a pH lower than its isoelectric point, without chaotrope, to avoid exposing the protein to potentially denaturing high pH values.

Many proteins, with pI values between pH 4 and pH 9, may be purified by binding to silicon carbide either at a binding pH below their pI or, in the presence of chaotrope, at a binding pH above their pI. Where either method is applicable, it may be more convenient to avoid chaotrope and use a binding pH below the pI.

When a protein is prepared by expression of a nucleotide sequence encoding the protein in a recombinant host cell, the expressed protein may become sequestered in inclusion bodies within the host cell, rather than being secreted into the medium. Sequestration of the expressed protein in inclusion bodies greatly complicates its purification and there remains a need for improved purification processes for such sequestered proteins.

In accordance with a further embodiment of the invention, a method is provided for recovering soluble recombinantly expressed protein from inclusion bodies. The method comprises releasing the protein from the inclusion bodies with a suitable solubilising agent, adjusting the solution to a binding pH and contacting the solution with silicon carbide to allow the protein to bind. The silicon carbide may be washed and the protein is eluted from the, silicon carbide at an elution pH. An elution pH of 11 to 12 is preferred.

Suitable solubilising agents include denaturing solubilising agents such as guanidinium isothiocyanate, guanidinium HCl and urea and non-denaturing solubilising agents such as sulphobetaines, including 3-(1-pyridino)-1-propane sulfonate and dimethylbenzylammonium propane sulfonate.

When guanidinium HCl is used as solubilising agent, at a concentration of 6 to 8M, it has been found that it is preferable to dilute the resulting solution of expressed protein, preferably in a stepwise manner, to a guanidinium HCl concentration of about 0.75M to 1M before contacting the solution, adjusted to a binding pH higher than the pI of the protein, with silicon carbide to bind the protein. The silicon carbide is preferably washed at the same pH, followed by elution of the protein at an elution pH.

Non-denaturing sulfobetaines may be added to a solution of expressed protein adjusted to a binding pH lower than the pI of the protein, to give a sulfobetaine concentration of 1 to 2M, and the solution is contacted with silicon carbide, followed by washing and elution as described above.

For use in the methods of the invention, any type of powdered silicon carbide powder may be used; preferred is silicon carbide of particle size in the range of about 5μ to about 20μ diameter. A particle size in the range of about 5.5μ to about 10μ is especially preferred.

EXAMPLES

The examples are described for the purposes of illustration and are not intended to limit the scope of the invention.

Methods of chemistry and protein and peptide biochemistry referred to but not explicitly described in this disclosure and examples are reported in the scientific literature and are well known to those skilled in the art.

Materials

Silicon Carbide

Silicon carbide 1000 or 1500 grade grit (Showa Denko, Osaka, Japan) was washed with a minimum of three changes of deionised, distilled water to remove dust and other extraneous materials and then sterilised by autoclaving. The sterilised material was stored at room temperature in water until required.

Aliquots are preferably removed for use under sterile conditions to reduce exposure of the silicon carbide to contaminants.

Binding Solution and Wash Solution

The binding solution was 50 mM sodium acetate, pH 4.5 to 7 or 50 mM Tris, pH 7 to 10. The binding solution was prepared as a 2-fold concentrate which was mixed with a protein solution in a one-to-one volume ratio.

Elution Solution

The elution solutions were 1 mM EDTA, 50 mM Tris, pH 11 to 12.

Example 1

Binding of Bovine Serum Albumin

Solutions of bovine serum albumin (molecular biology grade BSA: Sigma Aldrich) were prepared in buffers at various pH's by diluting a stock BSA solution (10 mg/mL in water) with an equal volume of 100 mM sodium acetate buffer at the required pH (pH 3.5, 4.0, 5.5, 6.0 or 7.0). Aliquots of silicon carbide were equilibrated to each of these pH's by washing the silicon carbide three times with sodium acetate buffer of the appropriate pH.

Each BSA solution was mixed in a plastic microfuge tube with silicon carbide equilibrated to the same pH to form a slurry at a ratio of 0.5 mg BSA:0.5 mg (dry weight) silicon carbide and the BSA was allowed to bind to the silicon carbide for 5 minutes at room temperature with no further mixing.

The slurry was then centrifuged for 1 minute at 1000×g followed by 4 minutes at 15000×g. The pelleted silicon carbide was washed once with sodium acetate buffer of the appropriate pH and re-pelleted by centrifugation under the same conditions.

The bound BSA was eluted from the silicon carbide by re-suspending the latter in 1 mL 10 mM Tris: 1mM EDTA, pH 12.0 and mixing briefly for 1 minute. After centrifugation at 15000×g, the eluate was removed. Recovered protein in the eluate was determined by spectrophotometry at 280 nm. FIG. 1 shows protein recovery at various binding pH's.

BSA recovery was optimal when binding to silicon carbide was carried out at a pH in the range of about 4.0 to about 5.0.

Example 2

Purification of BSA from Bovine Serum

Commercial bovine serum (CanSera Toronto, ON) normally used as supplement in cell culture media, was used to demonstrate the capability of silicon carbide to purify bovine serum albumin, using the conditions established in Example 1.

Bovine serum (0.2 ml) was diluted in sodium acetate buffer at pH 5 by mixing 1 part serum to 1 part of a two-fold concentrate buffer, and mixed by gentle stirring without allowing foam to form. The solution (0.4 ml) was then mixed with 0.5 gram of silicon carbide that had been prewashed with a buffer of matching pH and incubated at room temperature for 5 minutes. The mixing tube was centrifuged for 1 minute at 1,000×g and then for 4 minutes at 15,000×g to collect the pellet with bound protein. The pellet was then washed once with sodium acetate buffer of the appropriate pH and re-pelleted by centrifugation under the same conditions. Elution was at pH 7.5 or 12.0.

Figure 2:
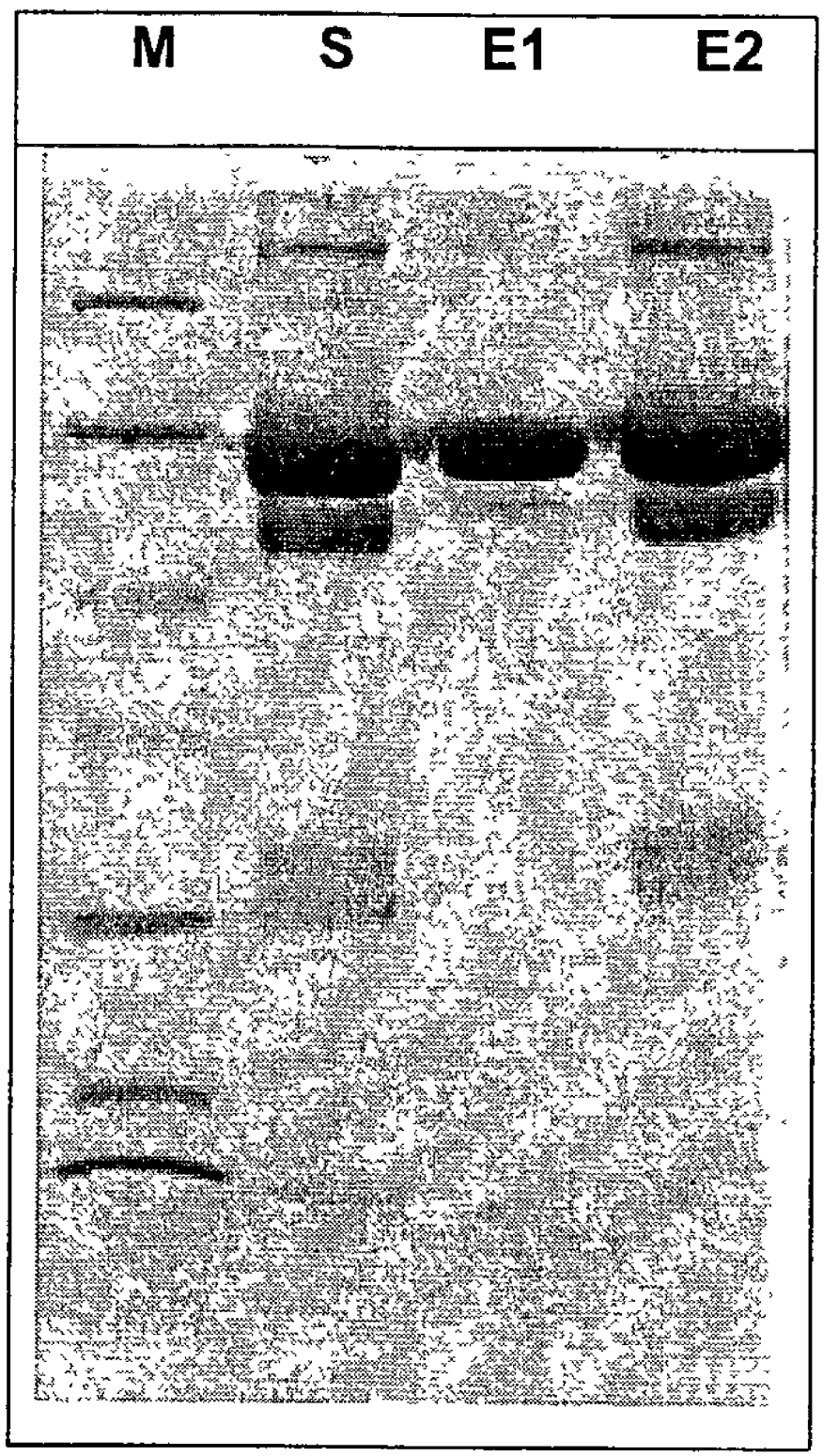
FIG. 2 shows a scan of an SDS-PAGE gel of whole bovine serum (Lane S), BSA purified by the method of the invention, with elution from silicon carbide at pH 7.5 (Lane E1) and proteins eluted at pH 12.0 (Lane E2), compared with standard molecular weight markers (Lane M).

FIG. 2 shows the results of the purification, as analyzed by SDS-PAGE. Bands were detected by Coomassie blue staining. Lane S contained whole serum. Serum contains up to 60% albumin, which appears as the most prominent band on SDS-PAGE; the molecular weight of BSA is 66 kilodalton. Lane E1 was purified albumin recovered by elution from silicon carbide at pH 7.5. Lane E2 was proteins recovered by elution at pH 12.0. Lane M was a molecular weight marker (New England Biolabs).

Example 3

Biological Activity of Enzyme Purified with Silicon Carbide

Figure 3:
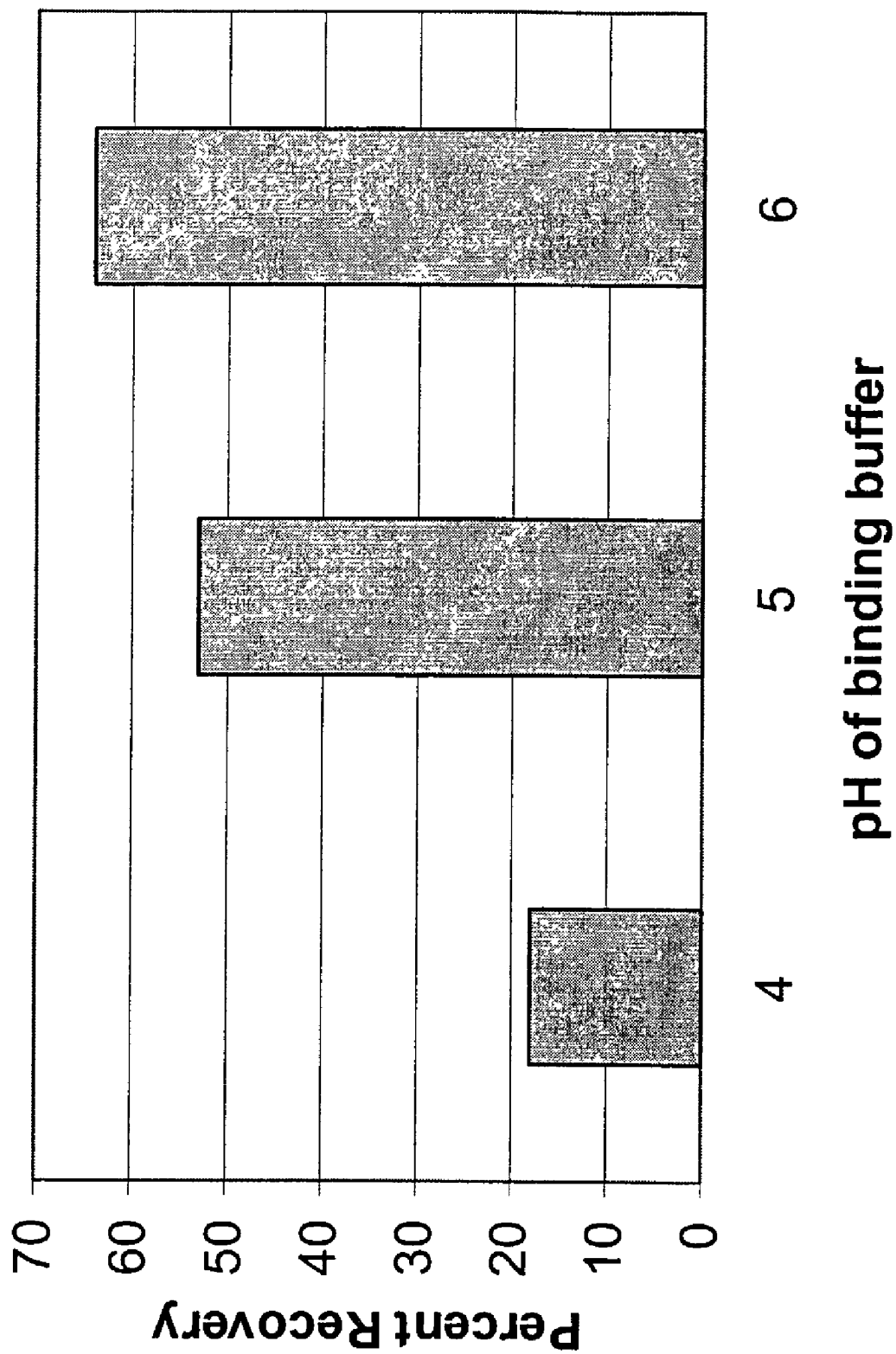
FIG. 3 shows the effect of binding pH on the recovery of a goat immunoglobulin/alkaline phosphatase conjugate from silicon carbide. Y axis shows % protein recovered, relative to total input amount.

The biological activity of alkaline phosphatase conjugated to a mixture of rabbit immunoglobulins (IgG+IgM; purchased from Jackson Laboratories; pI 5.8–7.3) was examined before and after binding and elution of the protein from silicon carbide. 50 μg aliquots of immunoglobulin/phosphatase conjugate were mixed with binding buffer at pH 4, 5 and 6 and contacted with 0.5 g silicon carbide in a spin column, followed by elution with elution solution. Protein recovery is shown in FIG. 3.

Figure 4:
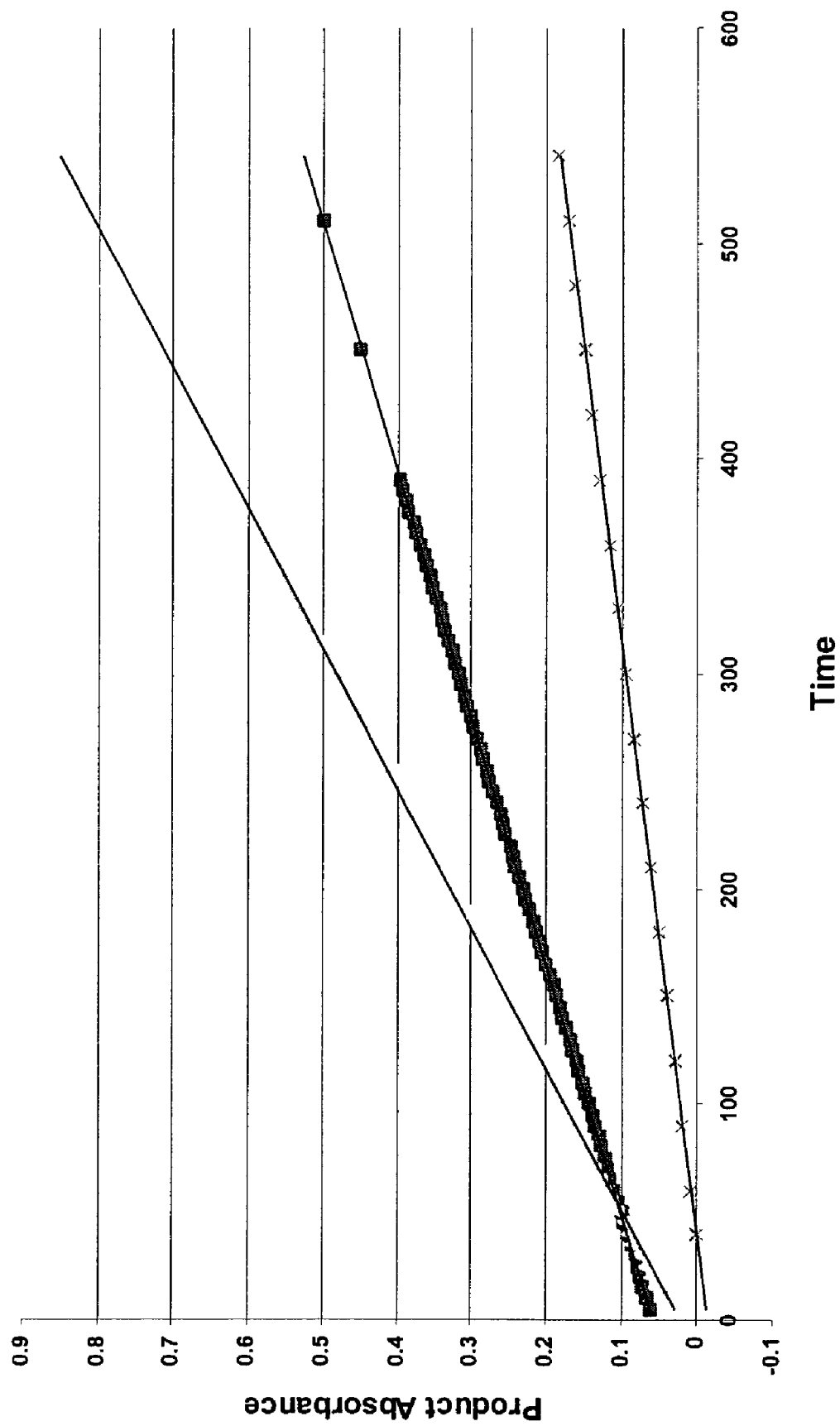
FIG. 4 shows alkaline phosphatase activity of an immunoglobulin/alkaline phosphatase conjugate recovered from silicon carbide after binding at pH 4 (▲), pH 5 (■) and pH 6 (X). Alkaline phosphatase activity is expressed as absorbance at 410 nm (Y axis) over time in minutes (X axis).

Alkaline phosphatase activity of the recovered alkaline phosphatase/immunoglobulin conjugate was determined using a standard colorimetric alkaline phosphatase assay (Sigma Immuno Chemicals, product N-2765). FIG. 4 shows the activity of the protein eluted after binding at pH 4 (■), pH 5 (▲), and pH 6 (X). The results show that all recovered proteins had activity, indicating that the purification process using silicon carbide preserves protein conformation and enzymatic activity.

Example 4

Recovery of Lysozyme Bound to Silicon Carbide at Various pH's

Figure 5:
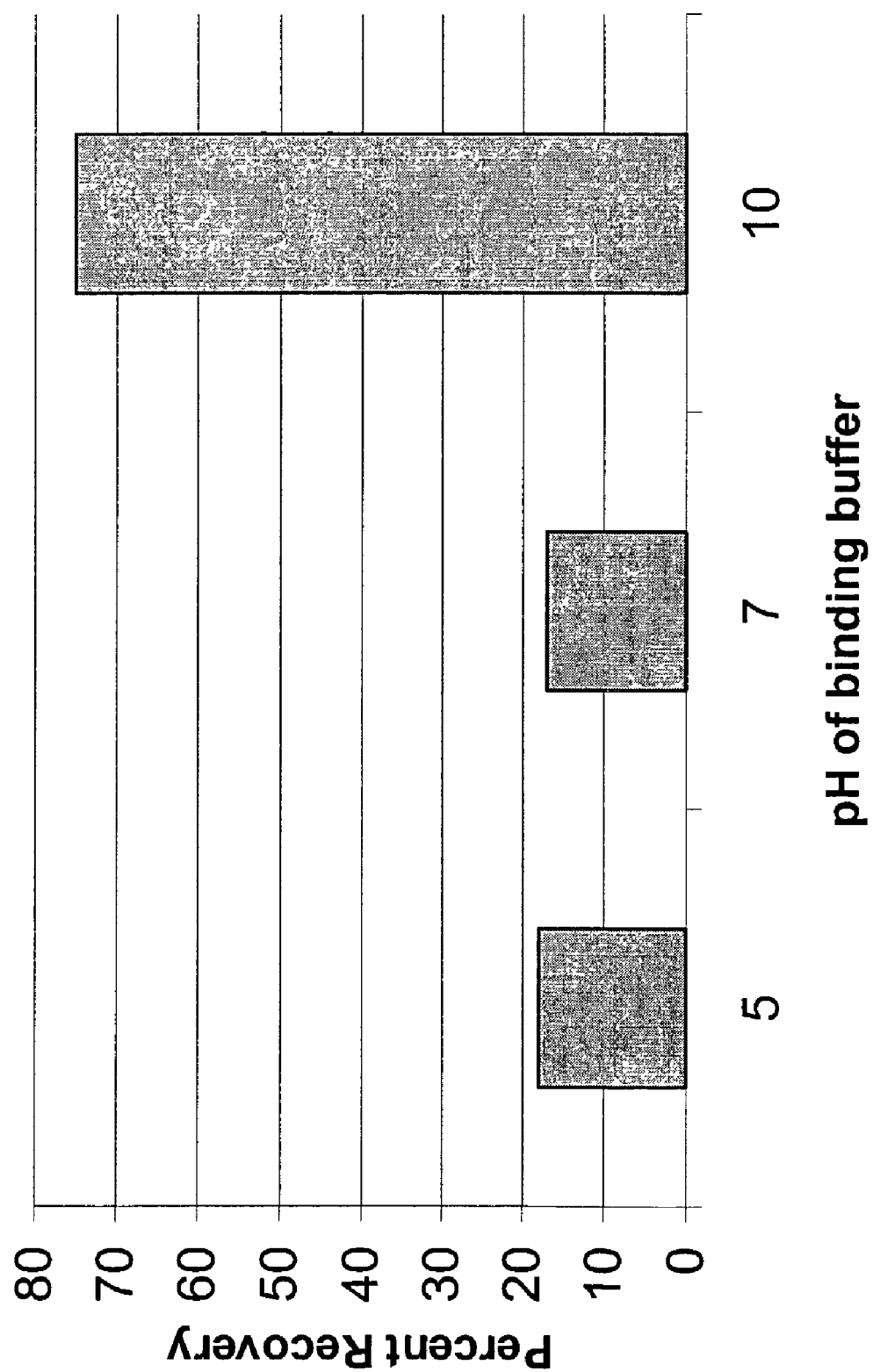
FIG. 5 shows % recovery of lysozyme by purification on silicon carbide after binding at the indicated pH.

Aliquots of chicken egg white lysozyme (pI 10.76) were dissolved in 50 mM sodium acetate buffer pH 5 or 7, or in 50 mM Tris buffer, pH 10, at a concentration of 1 mg/mL, and allowed to bind to silicon carbide at these pH's as described in Example 1. After washing with the same binding buffer, the protein was eluted at pH 12 as described in Example 1. The amount of protein recovered was determined by its spectrophotometric absorbancy at 280 nm wavelength. The results are shown in FIG. 5. Maximum recovery was seen when binding was carried out at pH 10.

Example 5

Binding Profiles of Three Proteins to Silicon Carbide

Figure 6:
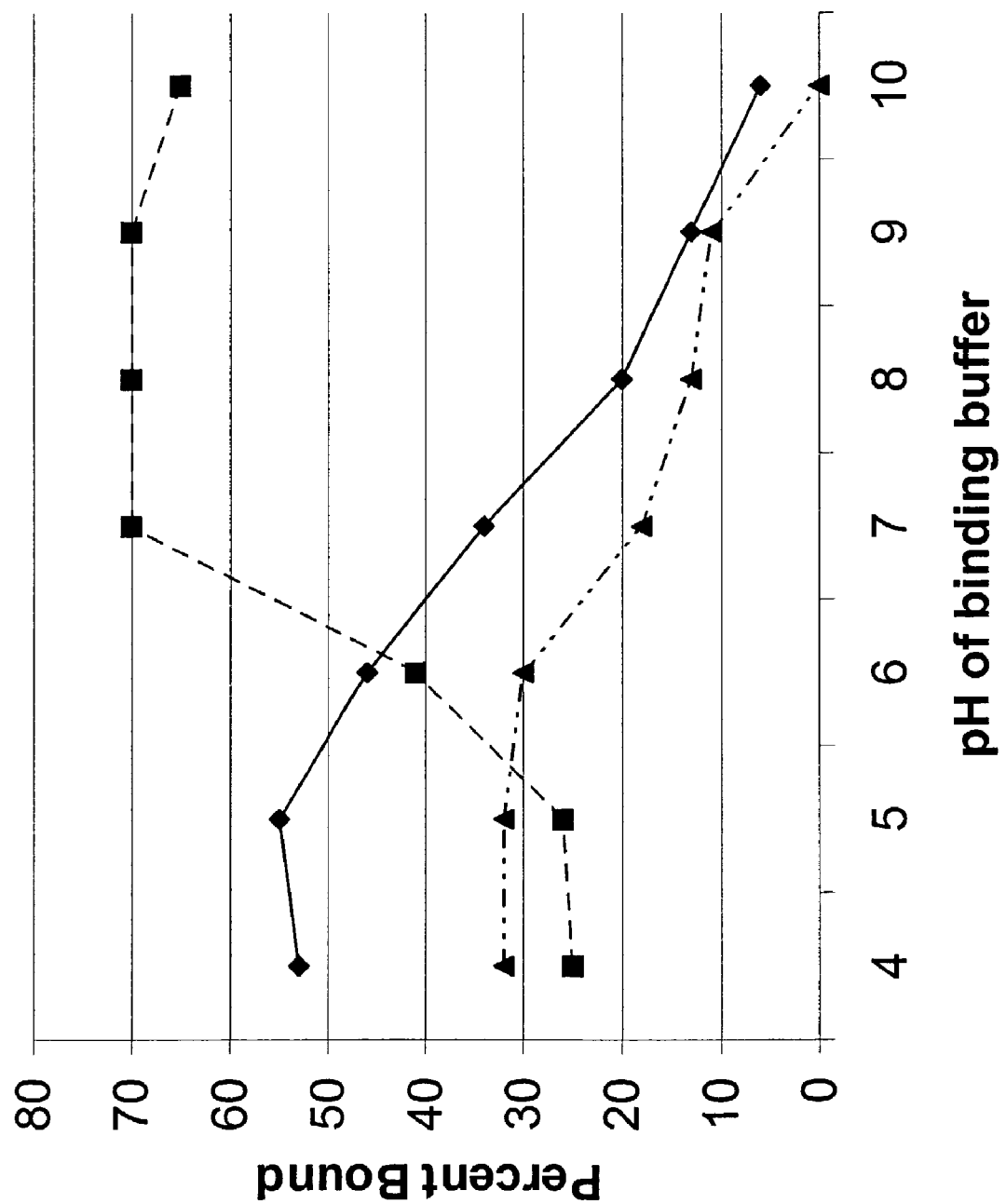
FIG. 6 shows percent binding of BSA (♦), lysozyme (■) and amylase (▲) to silicon carbide at indicated pH's.

Three proteins (bovine serum albumin (Sigma Aldrich), chicken egg white lysozyme (Sigma), and pancreatic porcine α-amylase (Sigma)) were individually bound to silicon carbide at various pH's, using the spin column technique. The amount bound was calculated as the difference between the input amount and the amount of protein that remained in flowthrough. The binding was done over pH range 4 to 10, with one pH unit increments. The binding profiles are shown in FIG. 6.

The net charge of bovine serum albumin (BSA), chicken egg white lysozyme and porcine amylase at various pH's was also calculated as described in Lehninger (supra), using the amino acid compositions of these proteins appearing in Genbank. This calculation can be conveniently carried out by the automated method provided by L'Atelier Bio Informatique de Marseille (A.B.I.M.), Universite de Provence, France at http://www.up.univ-mrs.fr/~wabim/d_abim/compo-p.html.

BSA: Genbank Accession No. CAA 76847; theoretical pI 5.71;

chicken egg white lysozyme: Genbank Accession No. 230896; predicted MW 14,313.07; theoretical pI 10.76;

porcine pancreatic α-amylase: Genbank Accession No. ALGP; predicted MW 55,474.89; apparent MW 50,000; theoretical pI 5.73.

Figure 7:
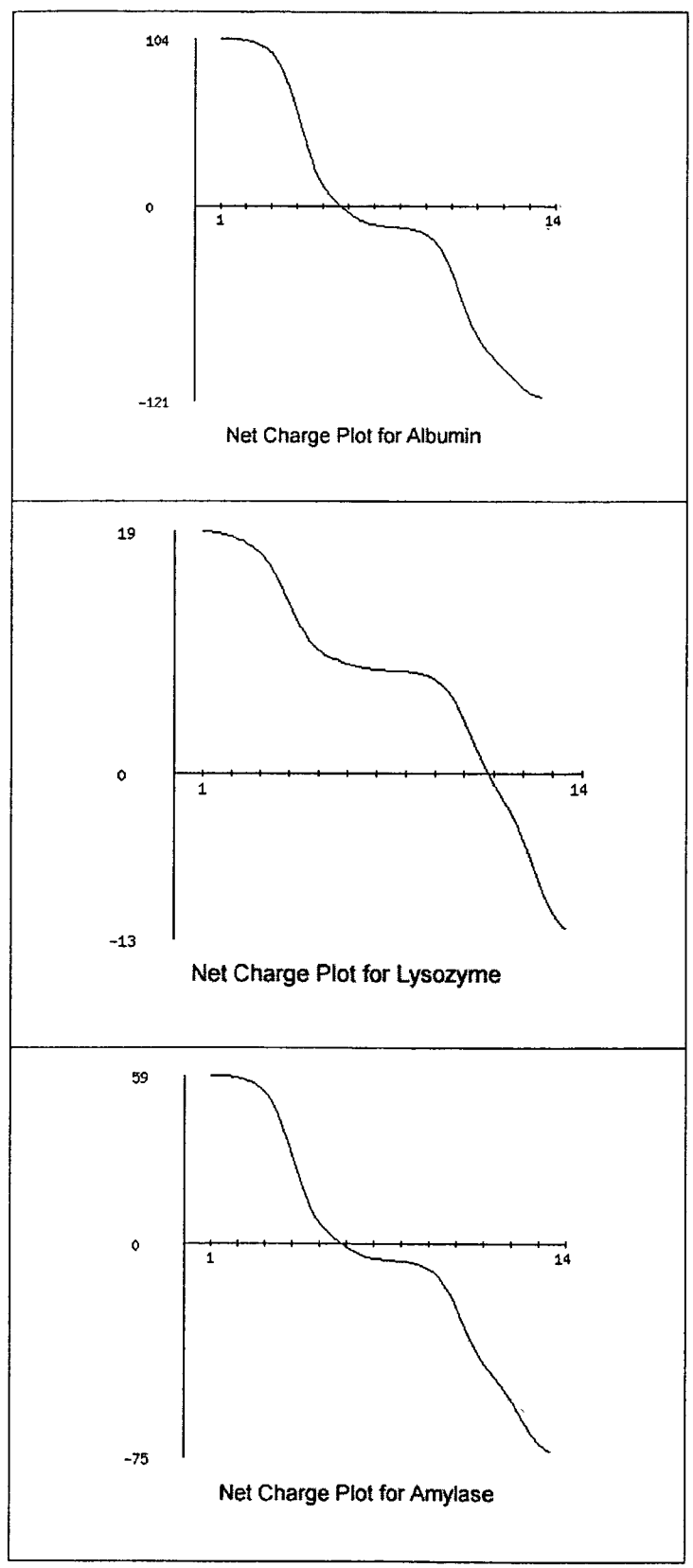
FIG. 7 shows calculated net charge profiles of BSA, lysozyme and amylase over pH range 1 to 14.

The calculated net charge profiles for these three proteins at various pH's are shown in FIG. 7. Comparison of this figure with the binding profiles of FIG. 6 demonstrated that protein binding to silicon carbide was optimal over the pH range in which the protein has a net positive charge, i.e. below the pI of the protein Example 6

Binding in Presence of a Chaotrope

Figure 8:
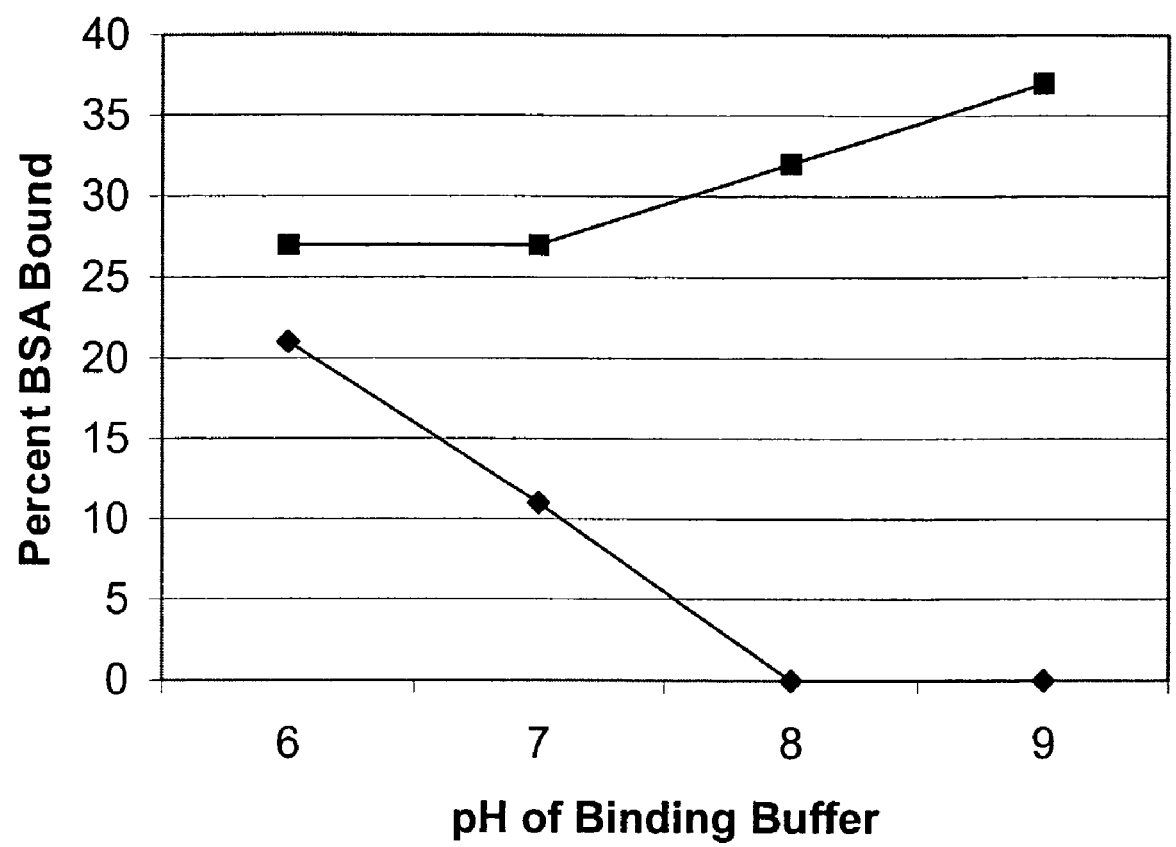
FIG. 8 shows % BSA bound to silicon carbide at various binding pHs in the presence (■) or absence (♦) of 0.75M guanidinium hydrochloride.

The binding of bovine serum albumin to silicon carbide at various pH's was examined in the presence or absence of the chaotrope, guanidinium hydrochloride (0.75M), using a spin column. As previously determined, binding of BSA to silicon carbide fell precipitously as the pH was raised above pH6. In contrast, as shown in FIG. 8, in the presence of the chaotrope, BSA binding to silicon carbide increased as the pH was raised above pH 7.

Example 7

Binding of Peptides

Poly-lysine (Sigma Aldrich: MW 3,100; approx. 23 lysine residues) and poly-arginine (Sigma Aldrich: MW 500; approx. 54 arginine residues) peptides have a high pI (predicted pI poly-lysine 11.2 and poly-arginine>13) and were found to bind to silicon carbide over a broad range of pH values.

Figure 9:
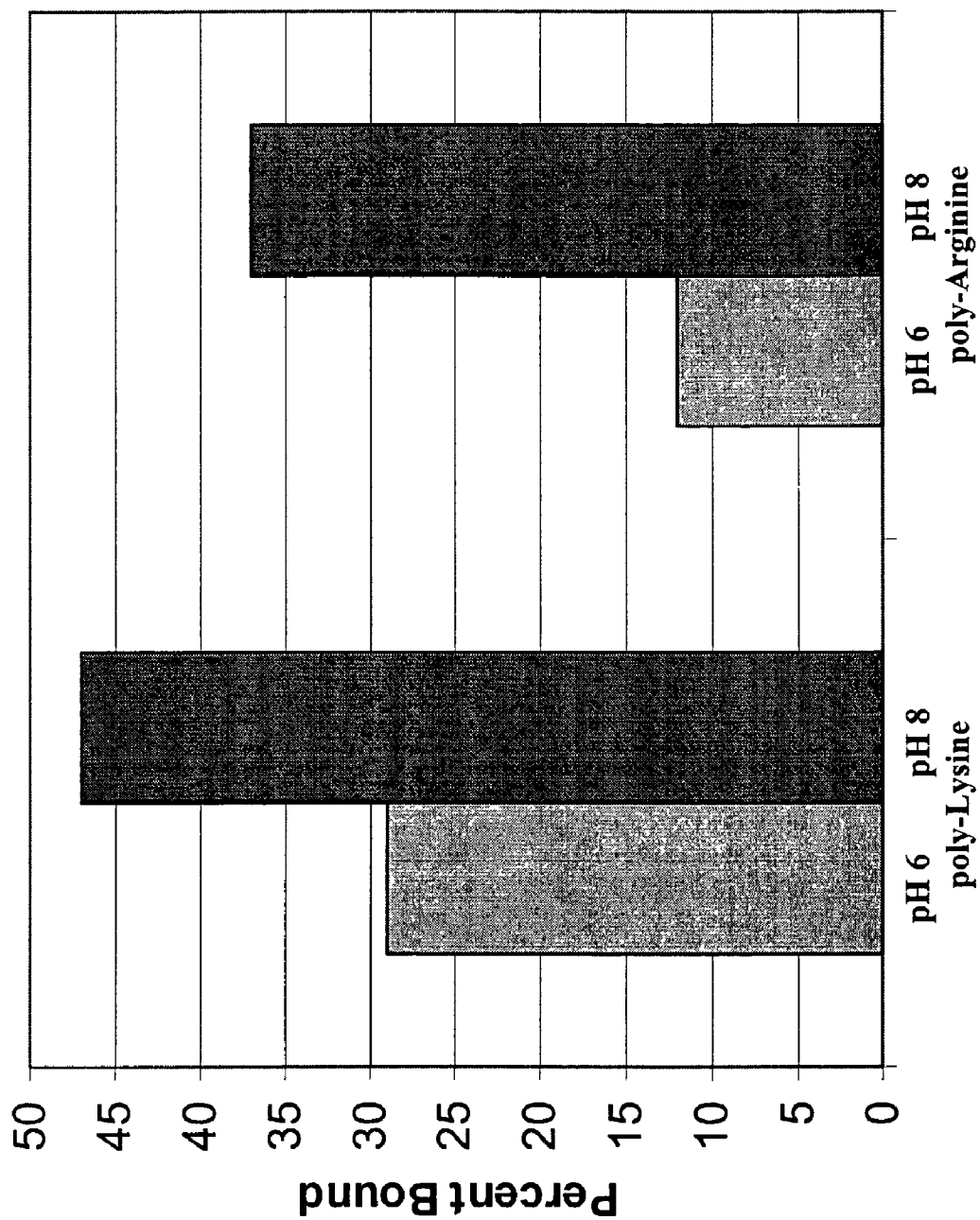
FIG. 9 shows % of peptide bound to silicon carbide at binding pH 6 or 8.

The peptides were dissolved in 50 mM sodium acetate pH 6.0 or 50 mM Tris pH 8.0 at a concentration of 10 mg/mL, and bound to silicon carbide in a spin column at a weight ratio of 0.5 mg peptide to 0.5 g silicon carbide. The net amount of bound peptides bound was determined using a colorimetric ninhydrin-based assay (Doi, E., Shibata, D., and Matoba, T., (1981), Modified Colorimetric Ninhydrin Methods for Peptidase Assay, Analytical Biochemistry 118: 173–184). FIG. 9 shows that, for either peptide, the fraction of total peptide bound is higher at pH 8 than at pH 6.

Figure 10:
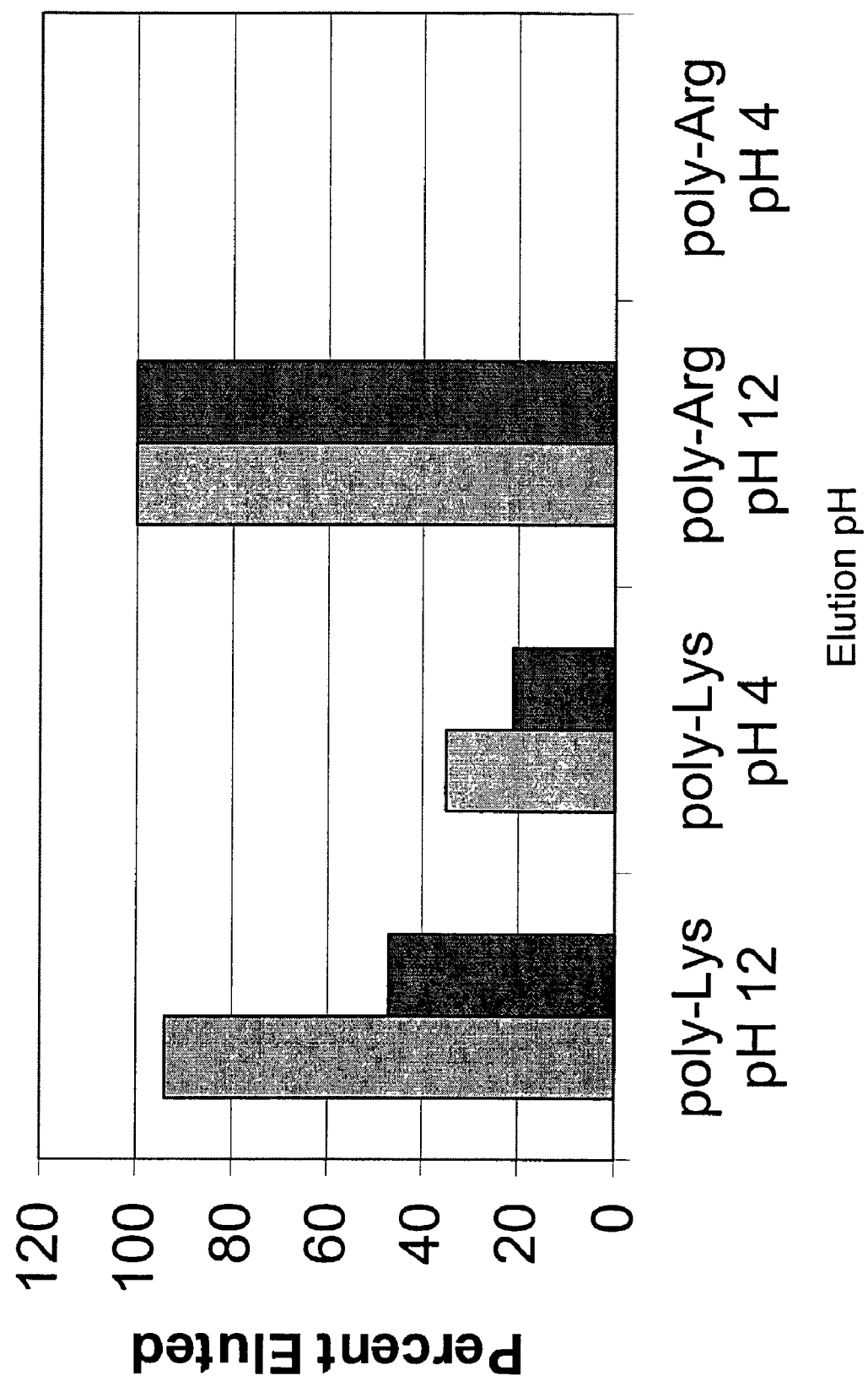
FIG. 10 shows % of peptide eluted from silicon carbide at elution pH 4 or 12, after binding at pH 6 (lighter shaded bars) or 8 (darker shaded bars).

The bound peptides were eluted at either pH 4 or 12. FIG. 10 shows that the amount of peptide eluted was consistently higher at pH 12.

Example 8

Purification of a Recombinant Protein from Inclusion Bodies

The purification of recombinantly expressed calf thymus ribonuclease A was carried out by binding to silicon carbide. The pI of the recombinant protein was calculated as described in Example 4, and found to be 6.4.

*Escherichia coli* cells carrying an expression vector encoding calf thymus ribonuclease A protein (constructed from sequence of Genbank Accession No 230917) were grown in 1 liter LB medium until A600 was 0.6–0.7 with induction of expression by IPTG. Control cultures were uninduced.

Bacterial cells from 1 liter of induced or uninduced culture were collected by centrifugation (10,000×g, 20 min, 4° C.) and resuspended in 50 ml of a wash solution (20 mM Tris, pH 7.5, 1 mM EDTA, 20% sucrose), followed by incubation on ice for 10 minutes. The cells were pelleted by centrifugation, then resuspended in 50 ml ice-cold water. The suspension was then incubated on ice for 10 minutes. The cells were again collected by centrifugation and resuspended in 10 ml of lysis buffer (phosphate-buffered saline containing 5 mM EDTA and 1×phenylmethylsulfonylfluoride (PMSF; Sigma-Aldrich). The suspension was subjected to 3 cycles of freezing in liquid $N_2$ and thawing quickly in a water bath at 42° C. The suspension was further treated by sonication (30-second pulses at 50W with 20-second pauses). Ten milliliters of DNAseI prepared at 40 micrograms/mL were added to the suspension for ten minutes. To the mixture, another 40 mL of the lysis buffer was then added to dilute the mixture.

The inclusion bodies were pelleted by centrifugation (16,000×g, 30 min, 4° C.) and the pellet was incubated for 10 minutes and washed with 40 mL of PBS containing 25% sucrose, 5 mM EDTa, 1% Triton-X. The inclusion bodies were pelleted by centrifugation and the wash process was repeated.

The washed pellet containing inclusion bodies was solubilized in 10 ml of 50 mM Tris.HCl pH 9.0 containing 8 M guanidinium HCl, 5 mM EDTA. The solution was centrifuged (16,000×g, 30 min, 4° C.) to remove insoluble particulates. The clarified solution was then diluted sequentially in three steps with 1 volume of 50 mM Tris.HCl, pH 9.0 so that the final concentration of guanidinium hydrochloride was 1 M. The resulting solution was applied to silicon carbide in a spin column at a ratio of 400 microliters of protein solution to 500 g of silicon carbide using the 'column' format of the purification method. The liquid phase was allowed to interact with the solid phase for 5 minutes at room temperature, then centrifuged on a benchtop microfuge at 15,000×g for 1 minute. The solid phase with bound proteins was washed once with 50 mM Tris.HCl pH 8.0 1 M guanidinium hydrochloride, followed by centrifugation, and once with the same buffer without guanidinium hydrochloride. The bound proteins were eluted with 100 microliters of 50 mM Tris, pH 12 by layering the elution buffer on the silicon carbide, followed by centrifugation.

Figure 11:
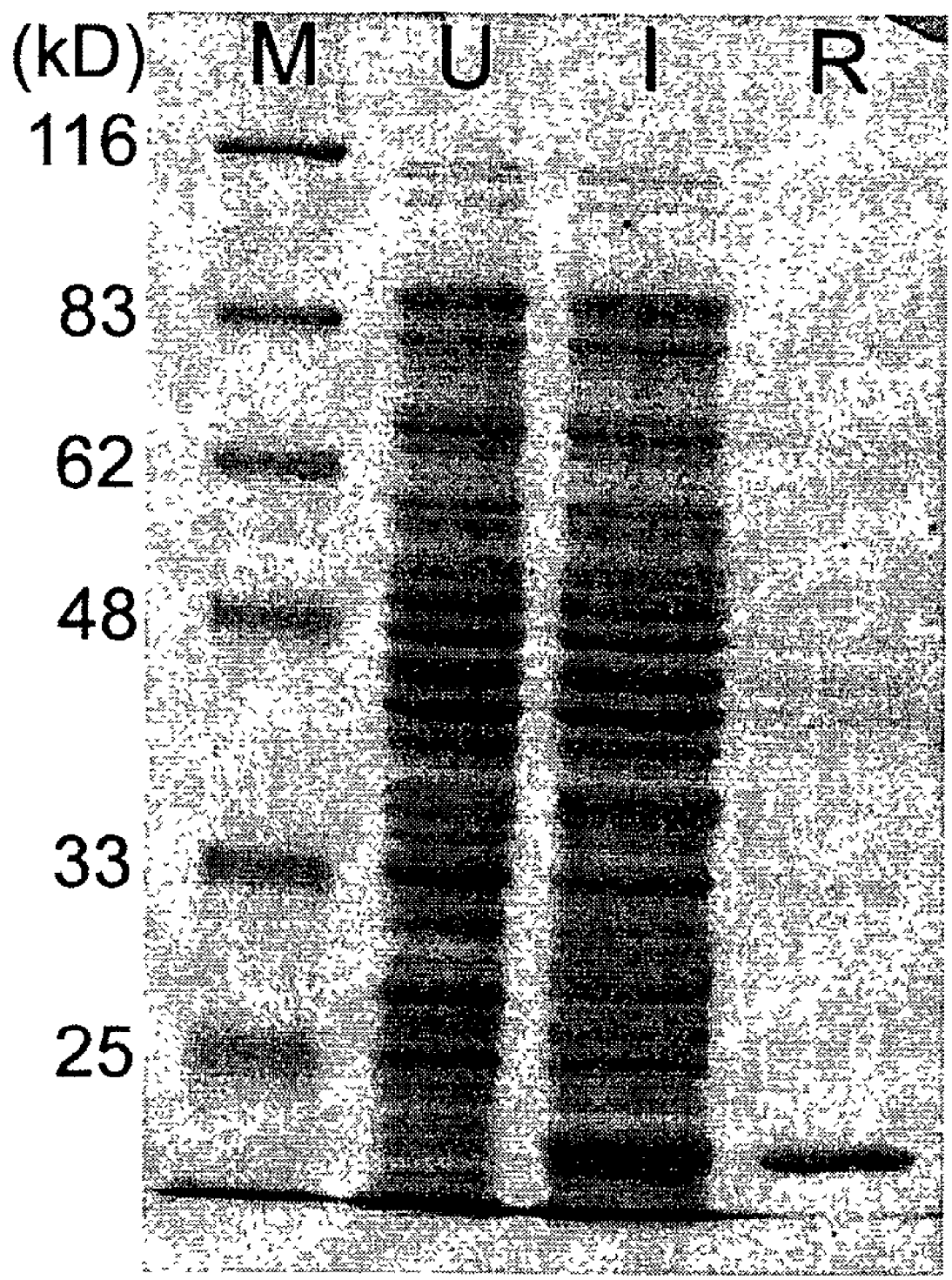
FIG. 11 shows a scan of an SDS-PAGE analysis of proteins from solubilised inclusion bodies from uninduced *E.coli* cells (Lane U) or cells induced to express ribonuclease A (Lane I), and ribonuclease A purified from induced cell inclusion bodies and purified on silicon carbide (MW 13.7 kDa Lane R), compared with standard molecular weight markers (Lane M).

SDS-PAGE with Coomassie blue staining (FIG. 11) was used to analyze solubilized inclusion bodies from uninduced cells (lane U) and induced cells (lane I), and purified ribonuclease A recovered from silicon carbide (lane R; molecular weight is 13.7 kilodaltons). The size of the molecular weight marker bands (lane M) are indicated. The recovered purified ribonuclease A band corresponds to the induced band seen in Lane I. The recovered enzyme showed normal RNAase A activity against *E.coli* RNA (data not shown).

Example 9

Figure 12:
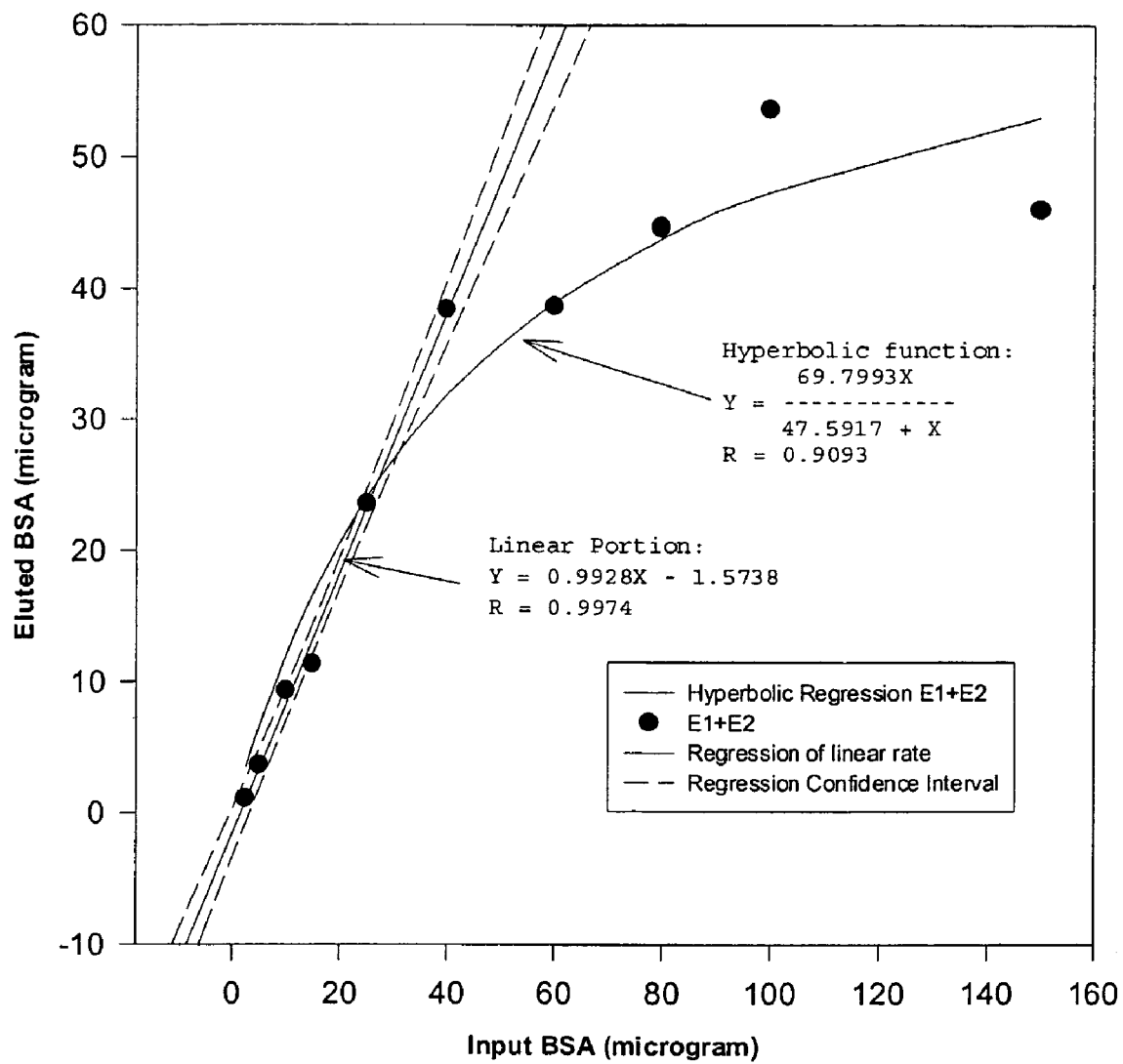
FIG. 12 shows BSA recovery from silicon carbide at various column loadings.

Spin columns (Axigen Scientific) were prepared containing 25 mg of silicon carbide (grit size 2500). Commercial BSA (Sigma) was dissolved in 50 mM sodium acetate, pH 4.5, at various concentrations and 250 μl aliquots of these solutions, containing 2.5, 5.0, 10.0, 15.0, 25.0, 40.0, 60.0, 80.0, 100.0 and 150.0 μg BSA respectively, were added to separate columns. Columns were spun at 15,000×g for 1 min, followed by two washes with the same acetate buffer, with centrifugation at each wash step. Columns were eluted twice with 25 μl 100 mM Tris, pH12 (designated elutions E1 and E2). The protein content of each eluate was determined by Bio-Rad protein assay and total protein recovery was calculated. The results are shown in Table 1 and FIG. 12.

TABLE 1

| BSA added to column (μg) | BSA recovered in E1 and E2 (μg) | % Protein Recovery |
|---|---|---|
| 2.5 | 1.1 | 45 |
| 5.0 | 3.6 | 72 |
| 10.0 | 9.3 | 93 |
| 15.0 | 11.3 | 76 |
| 25.0 | 23.5 | 94 |
| 40.0 | 38.4 | 96 |
| 60.0 | 38.6 | 64 |
| 80.0 | 44.6 | 56 |
| 100.0 | 53.6 | 54 |
| 150.0 | 46.0 | 31 |

The data points for input amount of BSA versus amount eluted (elutions 1 and 2 combined) were plotted. A typical hyperbolic curve was observed and the data points were fitted using the program Jandel SigmaPlot to obtain a correlation coefficient of 0.9093. The parameters of the hyperbolic regression are as shown on the graph. The initial dose response rate was determined by fitting the first 6 data points on the straight line and a correlation coefficient of 0.9974 was obtained.

The experiment shows that a high efficiency of recovery of bound BSA is obtained when the input amount is within the linear range of the columns.

Although preferred embodiments of the invention have been described herein in detail, it will be understood by those skilled in the art that variations may be made thereto without departing from the spirit of the invention.

I claim:

1. A method for recovering at least one protein or peptide from a solution, comprising:
   a) contacting the solution containing the at least one protein or peptide with silicon carbide at a binding pH for the at least one protein or peptide to allow the at least one protein or peptide to bind to the silicon carbide;
   b) exposing the silicon carbide of step (a) to an elution pH for the at least one protein of peptide to allow the at least one protein or peptide to be eluted from the silicon carbide into an eluate; and
   c) recovering the at least one protein or peptide from the eluate.

2. The method of claim 1, wherein the protein or peptide is a protein selected from the group consisting of serum albumin, lysozyme and immunoglobulin.

3. The method of claim 1 wherein the solution is contacted with the silicon carbide by preparing a slurry of the solution and the silicon carbide.

4. The method of claim 1 wherein the silicon carbide has a particle size in the range of about 5μ to about 20μ.

5. The method of claim 1 wherein the solution is contacted with the silicon carbide contained in a support.

6. The method of claim 5 wherein the support is a spin column.

7. The method of claim 1, wherein the binding pH is lower than the isoelectric point of the selected protein or peptide.

8. The method of claim 7 wherein the binding pH is at least about 0.5 pH units below the isoelectric point of the selected protein or peptide and greater than about pH 4.

9. The method of claim 7 wherein the protein or peptide is eluted at an elution pH of at least about one pH unit higher than the isoelectric point of the protein or peptide.

10. The method of claim 9 wherein the selected protein is serum albumin, the binding pH is pH 5.0 and the elution pH is pH 7.5.

11. The method of claim 9 wherein the protein or peptide has a pI greater than about pH 5.0.

12. The method of claim 1, wherein the solution containing the protein or peptide is contacted with silicon carbide in the presence of a chaotrope and wherein the binding pH is higher than the isoelectric point of the protein or peptide.

13. The method of claim 12 wherein the binding pH is at least about 0.5 pH units above the pI.

14. The method of claim 12 wherein the protein or peptide has a pI lower than about pH 5.0.

15. The method of claim 12 wherein the protein or peptide is a phosphoprotein.

16. The method of claim 1 wherein the solution comprises a cell lysate and the method is for recovering total proteins from the lysate.

17. The method of claim 16 wherein the binding pH is a pH lower than the isoelectric point of the proteins contained in the lysate.

18. The method of claim 17 wherein the binding pH is about pH 4.0.

19. The method of claim 17 wherein the elution pH is a pH higher than the isoelectric point of the proteins contained in the lysate.

20. The method of claim 19 wherein the elution pH is about pH 12.0.

21. The method of claim 1 wherein the at least one protein or peptide is a recombinant protein expressed in a recombinant host and sequestered in inclusion bodies and wherein the method comprises an initial step of contacting the inclusion bodies containing the recombinant protein with a solubilising agent to provide a solution containing the recombinant protein, followed by contacting the solution with the silicon carbide at a binding pH for the protein.

22. The method of claim 21 wherein the solubilising agent is a denaturing solubilising agent.

23. The method of claim 21 wherein the solubilising agent is urea.

24. The method of claim 21 wherein the solubilising agent is guanidinium isothiocyanate or guanidinium HCl and wherein the solution is diluted about 6 fold to about 10 fold before being contacted with silicon carbide.

25. The method of claim 21 wherein the solubilising agent is a non-denaturing solubilising agent.

26. The method of claim 21, wherein the solubilising agent is a sulfobetaine.

* * * * *